(12) United States Patent
Linhardt et al.

(10) Patent No.: US 9,044,075 B2
(45) Date of Patent: *Jun. 2, 2015

(54) CONTAINER

(71) Applicant: Google Inc., Mountain View, CA (US)

(72) Inventors: Jeffrey George Linhardt, Mountain View, CA (US); Daniel Barrows, Mountain View, CA (US)

(73) Assignee: Google Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/924,911

(22) Filed: Jun. 24, 2013

(65) Prior Publication Data

US 2014/0374286 A1  Dec. 25, 2014

(51) Int. Cl.

| A45C 11/04 | (2006.01) |
|---|---|
| A45C 11/00 | (2006.01) |
| B65D 77/08 | (2006.01) |
| A61B 5/145 | (2006.01) |
| B65D 25/08 | (2006.01) |
| A61B 3/10 | (2006.01) |
| A61B 5/1468 | (2006.01) |
| A61B 5/1486 | (2006.01) |
| A61B 5/00 | (2006.01) |

(52) U.S. Cl.
CPC .............. *A45C 11/005* (2013.01); *B65D 77/08* (2013.01); *A61B 3/101* (2013.01); *A61B 5/14507* (2013.01); *A61B 5/14532* (2013.01); *A61B 5/14542* (2013.01); *A61B 5/1468* (2013.01); *A61B 5/1486* (2013.01); *A61B 5/6803* (2013.01); *A61B 5/6821* (2013.01); *B65D 25/08* (2013.01); *B65D 2585/545* (2013.01)

(58) Field of Classification Search
CPC . A45C 11/046; A45C 11/005; B65D 81/3266
USPC ................ 206/5.1, 38, 205, 210, 219–221; 53/471; 134/901; 264/1.32; 600/318, 600/319
See application file for complete search history.

(56) References Cited

U.S. PATENT DOCUMENTS

| 4,543,882 | A | * | 10/1985 | Ryder et al. ................ 101/35 |
| 4,738,355 | A | | 4/1988 | Jobe |
| 5,053,208 | A | | 10/1991 | Seamons et al. |
| 5,515,964 | A | * | 5/1996 | Bauman .................... 206/5.1 |
| 5,853,085 | A | * | 12/1998 | Luttrell ..................... 206/5.1 |

(Continued)

FOREIGN PATENT DOCUMENTS

EP    1810934 B1    9/2008

OTHER PUBLICATIONS

Search Report and Written Opinion for PCT/US2014/043865 mailed Oct. 14, 2014.

*Primary Examiner* — Luan K Bui
(74) *Attorney, Agent, or Firm* — McDonnell Boehnen Hulbert & Berghoff LLP

(57) ABSTRACT

The present disclosure provides an apparatus including a first chamber containing an eye-mountable device. The apparatus may also include a second chamber containing an aqueous solution. The apparatus may also include a membrane positioned between the first chamber and the second chamber. The membrane may be configured to rupture based on application of a force to the apparatus. The ruptured membrane may allow the aqueous solution to engage with the eye-mountable device. The apparatus may also include a lid to seal one or more of the first chamber and the second chamber.

18 Claims, 11 Drawing Sheets

(56) References Cited

U.S. PATENT DOCUMENTS

| | | | |
|---|---|---|---|
| 6,681,127 B2 * | 1/2004 | March | 600/319 |
| 7,275,640 B2 | 10/2007 | Bourne et al. | |
| 7,357,248 B2 * | 4/2008 | Sivakumar et al. | 206/219 |
| 7,699,161 B2 * | 4/2010 | Tokarski et al. | 206/5.1 |
| 7,699,162 B2 | 4/2010 | Tokarski | |
| 7,809,417 B2 | 10/2010 | Abreu | |
| 2003/0045783 A1 | 3/2003 | March et al. | |
| 2004/0027536 A1 * | 2/2004 | Blum et al. | 351/168 |
| 2004/0112769 A1 * | 6/2004 | Perry | 206/219 |
| 2006/0213784 A1 | 9/2006 | Tokarski et al. | |
| 2010/0106128 A1 * | 4/2010 | Mao et al. | 604/411 |
| 2010/0113901 A1 * | 5/2010 | Zhang et al. | 600/319 |
| 2010/0126888 A1 * | 5/2010 | Lee | 206/219 |

* cited by examiner

CONTAINER

BACKGROUND

Unless otherwise indicated herein, the materials described in this section are not prior art to the claims in this application and are not admitted to be prior art by inclusion in this section.

A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose in a tear film of a user wearing the eye-mountable device). The body-mountable device may also be configured to monitor various other types of health-related information.

SUMMARY

In one embodiment, the present disclosure provides an apparatus including a first chamber containing an eye-mountable device. The apparatus may also include a second chamber containing an aqueous solution. The apparatus may also include a membrane positioned between the first chamber and the second chamber. The membrane may be configured to rupture based on application of a force to the apparatus. The ruptured membrane may allow the aqueous solution to engage with the eye-mountable device. The apparatus may also include a lid to seal one or more of the first chamber and the second chamber.

In another embodiment, the present disclosure provides an apparatus including a container having external surfaces and an opening. The apparatus may also include a membrane separating the container into a first chamber and a second chamber. The first chamber may contain an eye mountable device, and the second chamber may contain an aqueous solution. The membrane may be configured to rupture based on application of a force to the apparatus. The ruptured membrane may allow the aqueous solution to engage with the eye-mountable device. The apparatus may also include a lid configured to seal the opening of the container.

In yet another embodiment, the present disclosure provides a method including providing a container having an opening. The method may also include providing an eye-mountable device in a first chamber of the container. The method may also include providing an aqueous solution in a second chamber of the container. The method may also include providing a membrane to divide the container into the first chamber and the second chamber. The membrane may be configured to rupture based on application of a force to the container to enable the aqueous solution to engage with the eye-mountable device. The method may also include providing a lid configured to seal the opening of the container.

These as well as other aspects, advantages, and alternatives, will become apparent to those of ordinary skill in the art by reading the following detailed description, with reference where appropriate to the accompanying drawings.

DETAILED DESCRIPTION

Figure 1:
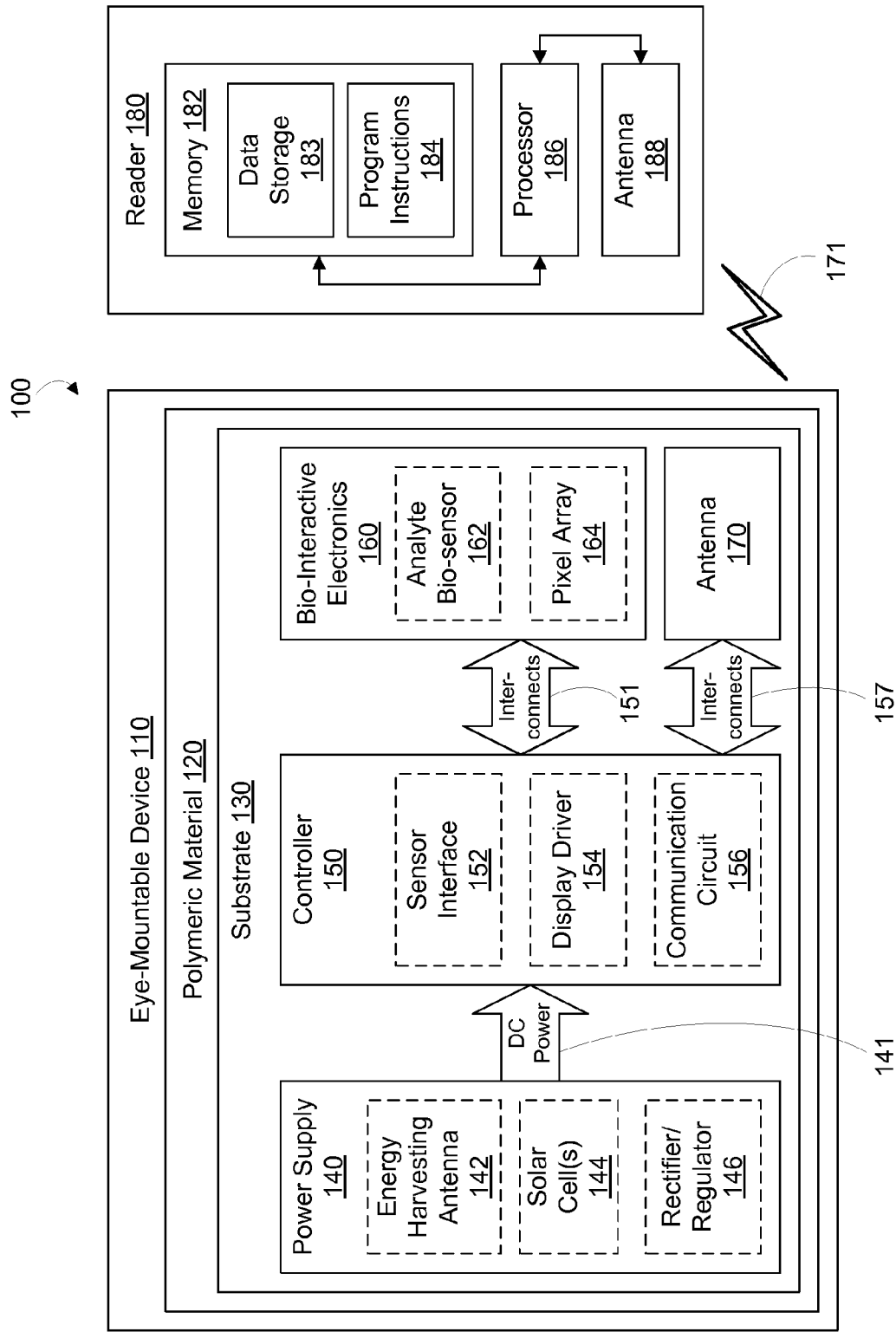
FIG. 1 is a block diagram of an example system that includes an eye-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A body-mountable device, such as a contact lens, may be configured to monitor health-related information based on at least one analyte detected in a fluid of a user wearing the body-mountable device. An example body-mountable device that comprises an eye-mountable device may include an embedded sensor configured to detect an analyte in a tear film of a user wearing the eye-mountable device, such as glucose. With such an arrangement, the analyte sensor may monitor health-related information, such as glucose level or corneal oxygen concentration. The example eye-mountable device will now be described in greater detail.

Such an eye-mountable device may need to be hydrated, sterilized and/or calibrated before insertion into a user's eye. However, long-term storage in an aqueous solution may cause problems with the various electronic components of the eye-mountable device. Thus, a packing device that separates an aqueous solution from the eye-mountable device may be desirable.

In one embodiment, the packaging for each eye-mountable device may include a two-chamber container. The first chamber may include the eye-mountable device. The second chamber may contain an aqueous solution. In one embodiment, the first and second chambers are arranged in a side-by-side configuration. In another embodiment, the first and second chambers are arranged in a top-bottom configuration.

In one embodiment, the aqueous solution in the second chamber may be a preconditioning solution used to hydrate the eye-mountable device before insertion into a user's eye. In another embodiment, the aqueous solution may be a sterilization and/or disinfecting solution. In yet another embodiment, the aqueous solution may be a calibration solution used to calibrate the analyte sensor on the eye-mountable device. Other potential aqueous solutions are possible as well.

The first and second chambers may be separated by a breakable membrane. The membrane may include a thin polymeric material. In use, the membrane may be ruptured to allow the aqueous solution to interact with the eye-mountable device. In one embodiment, the membrane may be ruptured by squeezing the container. In another embodiment, the membrane may be connected to a lid of the container, and the membrane may be ruptured when a user removes the lid of the container. In yet another embodiment, the membrane may be ruptured by shaking the container. Other embodiments of rupturing the membrane are possible as well.

It should be understood that the above examples of the apparatus are provided for illustrative purposes, and should not be construed as limiting.

II. Example Systems And Devices

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more bio-compatible materials, such as those employed for use in contact lenses or other ophthalmic applications involving direct contact with the corneal surface. The polymeric material 120 can optionally be formed in part from such bio-compatible materials or can include an outer coating with such bio-compatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of resists, masks, and deposition techniques can be employed to pattern materials on the substrate 130. The substrate 130 can be a relatively rigid material, such as polyethylene terephthalate ("PET") or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in the center region of the eye-mountable device 110. The bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display driver instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOD") proximal to the working electrode can catalyze glucose into hydrogen peroxide ($H_2O_2$). The hydrogen peroxide can then be oxidized at the working electrode, which releases electrons to the working electrode, resulting in an amperometric current that can be measured through the working electrode.

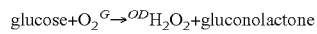

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivably by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earring, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 180 (e.g., via the communication circuit 156). The sensor reading can be communicated by, for example, modulating an impedance of the communication antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 2A:
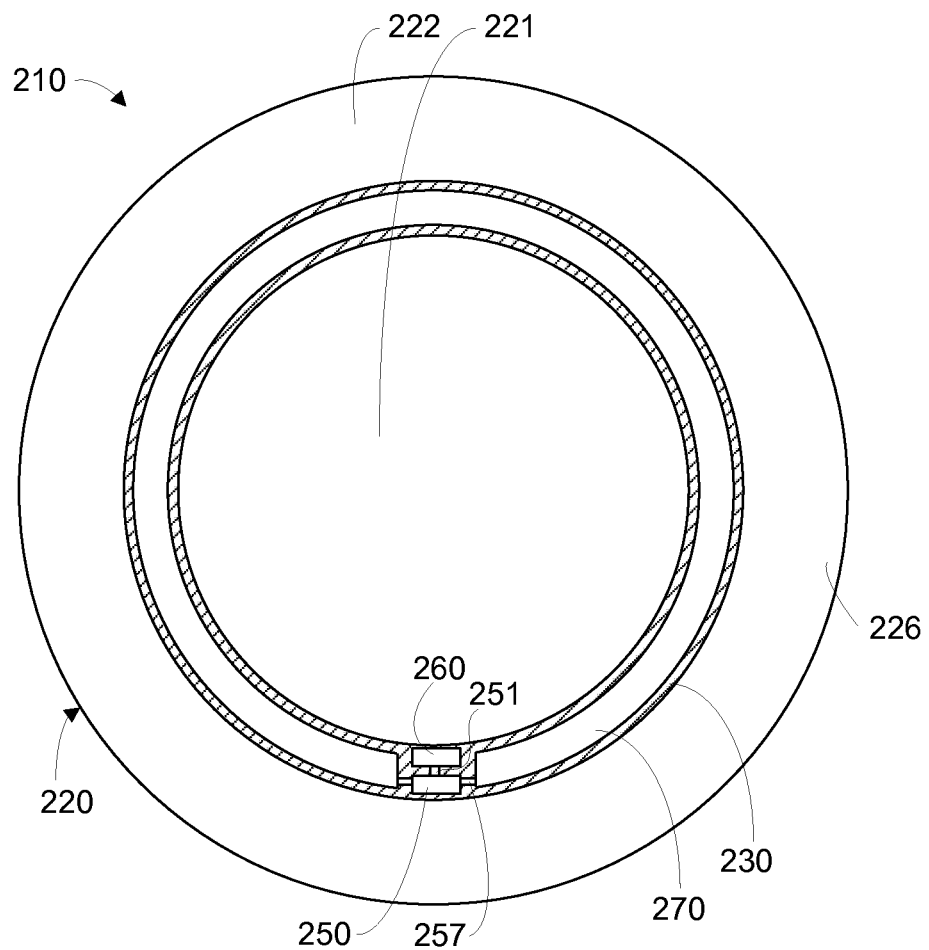
FIG. 2A is a bottom view of an example eye-mountable device.
Figure 2B:
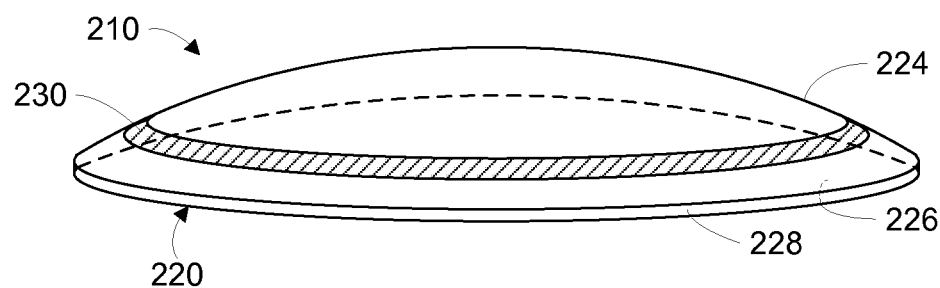
FIG. 2B is an aspect view of the example eye-mountable device shown in FIG. 2A.

FIG. 2A is a bottom view of an example eye-mountable device 210. FIG. 2B is an aspect view of the example eye-mountable device 210. It is noted that relative dimensions in FIGS. 2A and 2B are not necessarily to scale, but have been rendered for purposes of explanation only in describing the arrangement of the example eye-mountable device 210.

The eye-mountable device 210 may include a polymeric material 220, which may be a substantially transparent material to allow incident light to be transmitted to the eye. The polymeric material 220 may include one or more bio-compatible materials similar to those employed to form vision correction and/or cosmetic contact lenses in optometry, such as polyethylene terephthalate ("PET"), polymethyl methacrylate ("PMMA"), polyhydroxyethylmethacrylate ("poly-HEMA"), silicone hydrogels, or any combinations of these. Other polymeric materials may also be envisioned. The polymeric material 220 may include materials configured to moisturize the corneal surface, such as hydrogels and the like. In some embodiments, the polymeric material 220 is a deformable ("non-rigid") material to enhance wearer comfort.

To facilitate contact-mounting, the eye-mountable device 210 may comprise a concave surface 226 configured to adhere ("mount") to a moistened corneal surface (e.g., by capillary forces with a tear film coating the corneal surface). The bottom view in FIG. 2A faces the concave surface 226. While mounted with the concave surface against the eye, a convex surface 224 of eye-mountable device 210 is formed so as not to interfere with eye-lid motion while the eye-mountable device 210 is mounted to the eye. From the bottom view shown in FIG. 2A, an outer periphery 222, near the outer circumference of the eye-mountable device 210 has a concave curve shape, whereas a central region 221, near the center of the eye-mountable device 210, has a convex curve shape.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 may be selected according to the size and/or shape of the corneal surface of the wearer's eye. In some embodiments, the eye-mountable device 210 is shaped to provide a predetermined, vision-correcting optical power, such as provided by a prescription contact lens.

A sensing platform 230 is embedded in the eye-mountable device 210. The sensing platform 230 can be embedded to be situated near or along the outer periphery 222, away from the central region 221. Such a position ensures that the sensing platform 230 will not interfere with a wearer's vision when the eye-mountable device 210 is mounted on a wearer's eye, because it is positioned away from the central region 221 where incident light is transmitted to the eye-sensing portions of the eye. Moreover, portions of the sensing platform 230 can be formed of a transparent material to further mitigate effects on visual perception.

The sensing platform 230 may be shaped as a flat, circular ring (e.g., a disk with a centered hole). The flat surface of the sensing platform 230 (e.g., along the radial width) allows for mounting electronics such as chips (e.g., via flip-chip mounting) and for patterning conductive materials to form electrodes, antenna(e), and/or interconnections. The sensing platform 230 and the polymeric material 220 may be approximately cylindrically symmetric about a common central axis. The sensing platform 230 may have, for example, a diameter of about 10 millimeters, a radial width of about 1 millimeter (e.g., an outer radius 1 millimeter greater than an inner radius), and a thickness of about 50 micrometers. These dimensions are provided for example purposes only, and in no way limit the present disclosure.

A loop antenna 270, controller 250, and bio-interactive electronics 260 are included in the sensing platform 230. The controller 250 may be a chip including logic elements configured to operate the bio-interactive electronics 260 and the loop antenna 270, and may be the same as or similar to the controller 150 discussed in connection with FIG. 1. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) may be formed from any type of conductive material and may be patterned by any process that be used for patterning such materials, such as deposition or photolithography, for example. The conductive materials patterned on the substrate 230 may be, for example, gold, platinum, palladium, titanium, carbon, aluminum, copper, silver, silver-chloride, conductors formed from noble materials, metals, or any combinations of these materials. Other materials may also be envisioned.

Figure 2D:
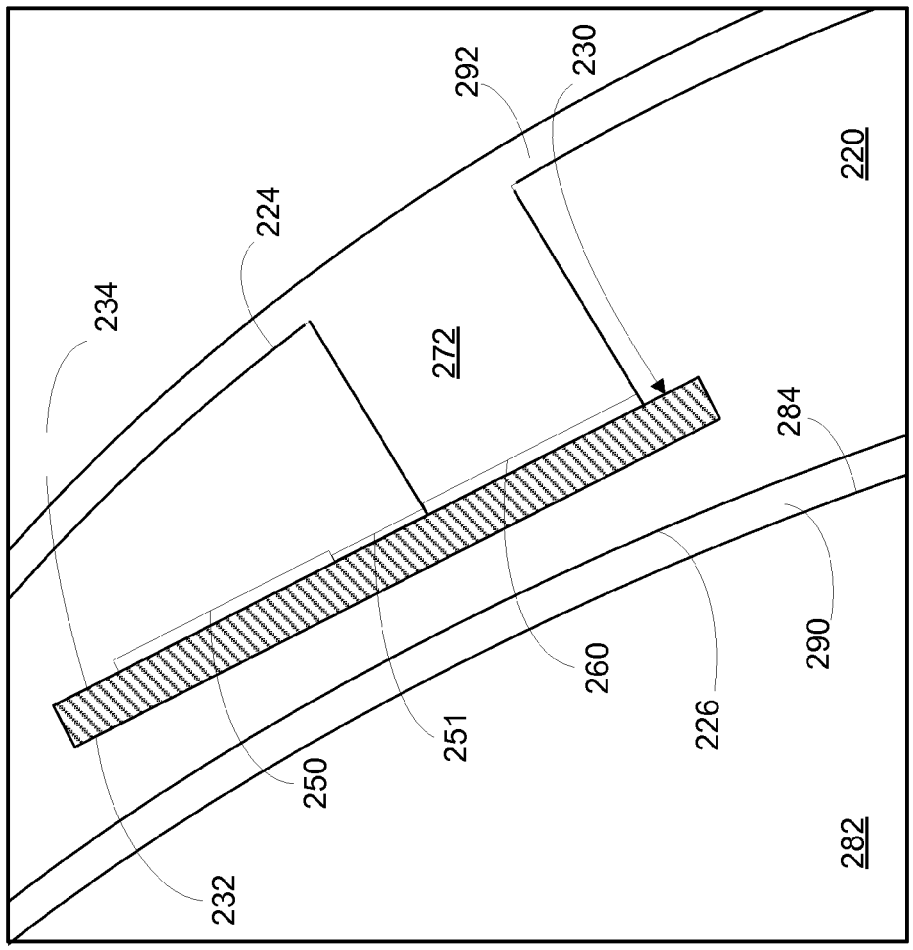
FIG. 2D is a side cross-section view enhanced to show the tear film layers surrounding the surfaces of the example eye-mountable device when mounted as shown in FIG. 2C.

As shown in FIG. 2A, the bio-interactive electronics module 260 is on a side of the sensing platform 230 facing the convex surface 224. Where the bio-interactive electronics module 260 includes an analyte bio-sensor, for example, mounting such a bio-sensor on the sensing platform 230 to be close to the convex surface 224 allows the bio-sensor to sense analyte that has diffused through convex surface 224 or has reached the bio-sensor through a channel in the convex surface 224 (FIGS. 2C and 2D show a channel 272).

The loop antenna 270 is a layer of conductive material patterned along the flat surface of the substrate 230 to form a flat conductive ring. The loop antenna 270 may be the same as or similar to the antenna 170 described in connection with FIG. 1. In some example embodiments, the loop antenna 270 does not form a complete loop. For example, the loop antenna 270 may include a cutout to allow room for the controller 250 and bio-interactive electronics 260, as illustrated in FIG. 2A. However, in another example embodiment, the loop antenna 270 can be arranged as a continuous strip of conductive material that wraps entirely around the sensing platform 230 one or more times. Interconnects between the ends of such a wound antenna (e.g., the antenna leads) can connect to the controller 250 in the sensing platform 230.

The sensing platform 230 may be a bio-compatible structure in which some or all of the components are encapsulated by a bio-compatible material. In one example, controller 250, interconnects 251, 257, bio-interactive electronics 260, and antenna 270 are fully encapsulated by bio-compatible material, except for the sensor electrodes in the bio-interactive electronics 260.

Figure 2C:
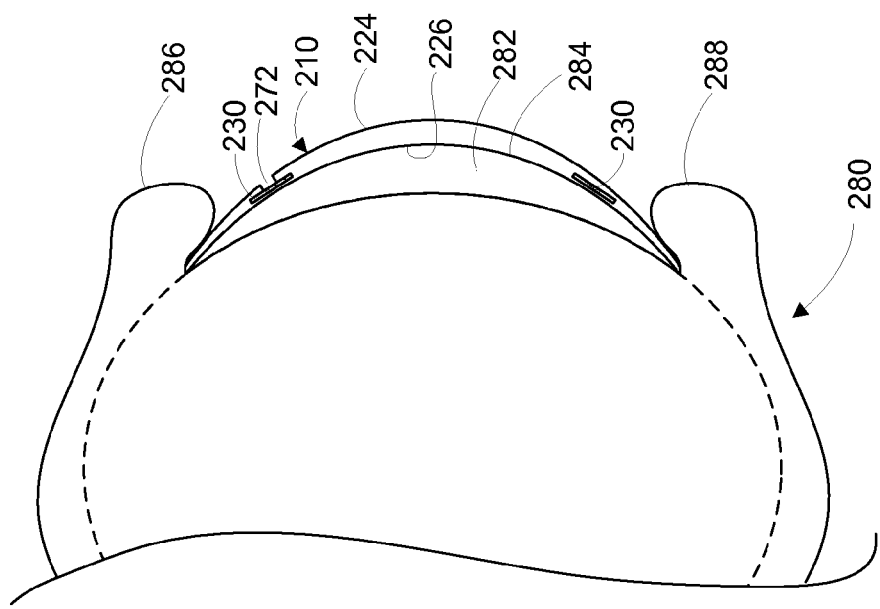
FIG. 2C is a side cross-section view of the example eye-mountable device shown in FIGS. 2A and 2B while mounted to a corneal surface of an eye.

FIG. 2C is a side cross-section view of the example eye-mountable electronic device 210 mounted to a corneal surface 284 of an eye 280. FIG. 2D is an enlarged partial view the cross-section of the example eye-mountable device shown in FIG. 2C. It is noted that relative dimensions in FIGS. 2C and 2D are not necessarily to scale, but have been rendered for purposes of explanation only in describing the arrangement of the example eye-mountable electronic device 210. Some aspects are exaggerated to allow for illustration and to facilitate explanation.

The eye 280 includes a cornea 282 that is covered by bringing an upper eyelid 286 and a lower eyelid 288 together over the surface of the eye 280. Incident light is received by the eye 280 through the cornea 282, where light is optically directed to light sensing elements of the eye 280 to stimulate visual perception. The motion of the upper and lower eyelids 286, 288 distributes a tear film across the exposed corneal surface 284 of the eye 280. The tear film is an aqueous solution secreted by the lacrimal gland to protect and lubricate the eye 280. When the eye-mountable device 210 is mounted in the eye 280, the tear film coats both the concave and convex surfaces 224, 226, providing an inner layer 290 (along the concave surface 226) and an outer layer 292 (along the convex surface 224). The inner layer 290 on the corneal surface 284 also facilitates mounting the eye-mountable device 210 by capillary forces between the concave surface 226 and the corneal surface 284. In some embodiments, the eye-mountable device 210 can also be held over the eye 280 in part by vacuum forces against the corneal surface 284 due to the curvature of the concave surface 226. The tear film layers 290, 292 may be about 10 micrometers in thickness and together account for about 10 microliters of fluid.

The tear film is in contact with the blood supply through capillaries in the structure of the eye and includes many biomarkers found in blood that are analyzed to diagnose health states of an individual. For example, tear film includes glucose, calcium, sodium, cholesterol, potassium, other biomarkers, etc. The biomarker concentrations in tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body.

As shown in the cross-sectional views in FIGS. 2C and 2D, the sensing platform 230 can be inclined so as to be approximately parallel to the adjacent portion of the convex surface 224. As described above, the sensing platform 230 is a flattened ring with an inward-facing surface 232 (closer to the concave surface 226 of the polymeric material 220) and an outward-facing surface 234 (closer to the convex surface 224). The sensing platform 230 can include electronic components and/or patterned conductive materials adjacent to either or both surfaces 232, 234.

As shown in FIG. 2D, the bio-interactive electronics 260, the controller 250, and the conductive interconnect 251 are mounted on the outward-facing surface 234 such that the bio-interactive electronics 260 are facing the convex surface 224. With this arrangement, the bio-interactive electronics 260 can receive analyte concentrations in the tear film 292 through the channel 272. However, in other examples, the bio-interactive electronics 260 may be mounted on the inward-facing surface 232 of the sensing platform 230 such that the bio-interactive electronics 260 are facing the concave surface 226.

III. An Ophthalmic Electrochemical Analyte Sensor

Figure 3:
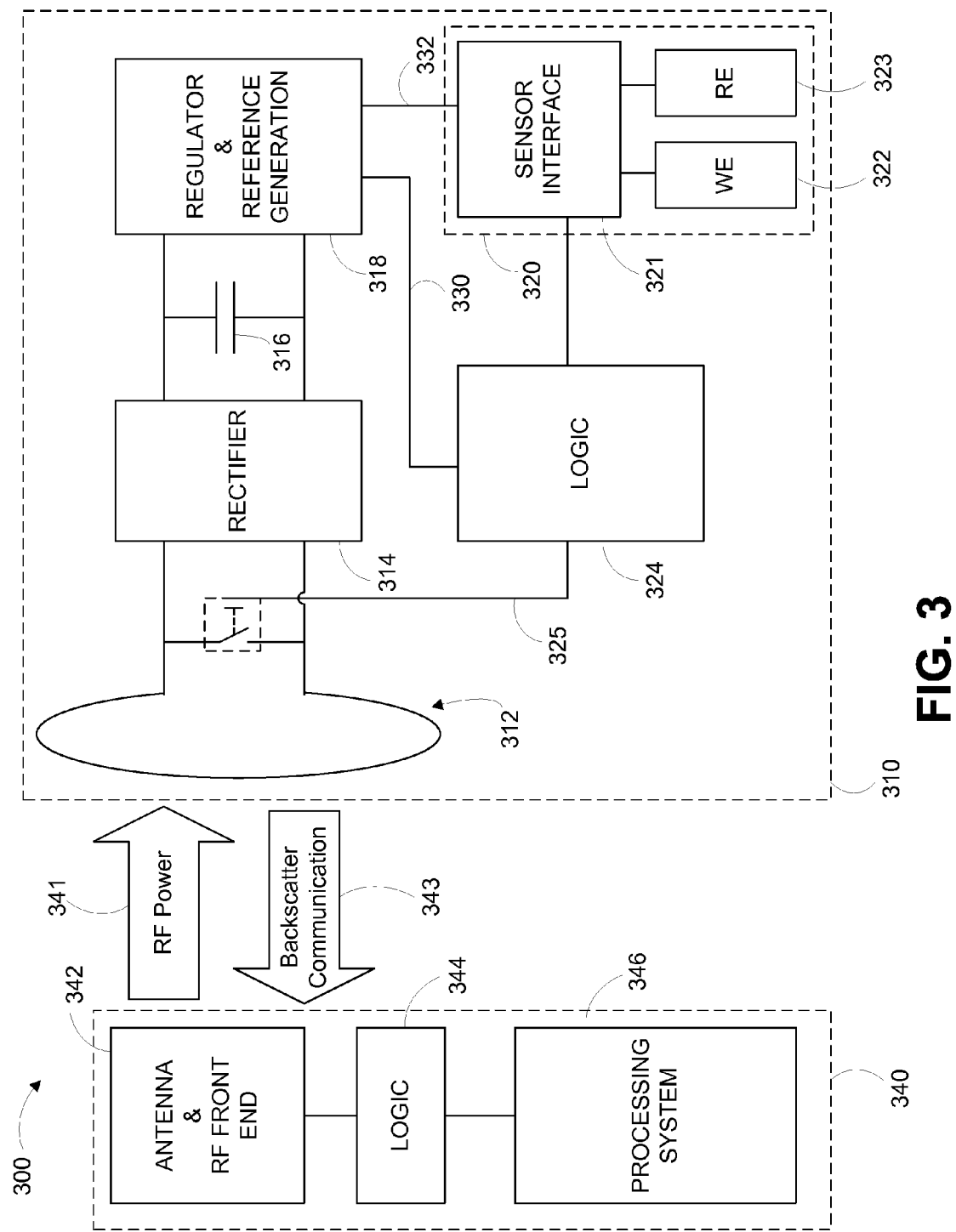
FIG. 3 is a functional block diagram of an example system for electrochemically monitoring a tear film analyte concentration.

FIG. 3 is a functional block diagram of a system 300 for electrochemically measuring a tear film analyte concentration. The system 300 includes an eye-mountable device 310 with embedded electronic components powered by an external reader 340. The eye-mountable device 310 includes an antenna 312 for capturing radio frequency radiation 341 from the external reader 340. The eye-mountable device 310 includes a rectifier 314, an energy storage 316, and regulator 318 for generating power supply voltages 330, 332 to operate the embedded electronics. The eye-mountable device 310 includes an electrochemical sensor 320 with a working electrode 322 and a reference electrode 323 driven by a sensor interface 321. The eye-mountable device 310 includes hardware logic 324 for communicating results from the sensor 320 to the external reader 340 by modulating (325) the impedance of the antenna 312. Similar to the eye-mountable devices 110, 210 discussed above in connection with FIGS. 1 and 2, the eye-mountable device 310 can include a mounting substrate embedded within a polymeric material configured to be mounted to an eye. The electrochemical sensor 320 can be situated on a mounting surface of such a substrate proximate the surface of the eye (e.g., corresponding to the bio-interactive electronics 260 on the inward-facing side 232 of the substrate 230) to measure analyte concentration in a tear film layer interposed between the eye-mountable device 310 and the eye (e.g., the inner tear film layer 40 between the eye-mountable device 210 and the corneal surface 22).

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter high frequency noise on the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the external reader 340 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or a network-connected memory.

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

Figure 4A:
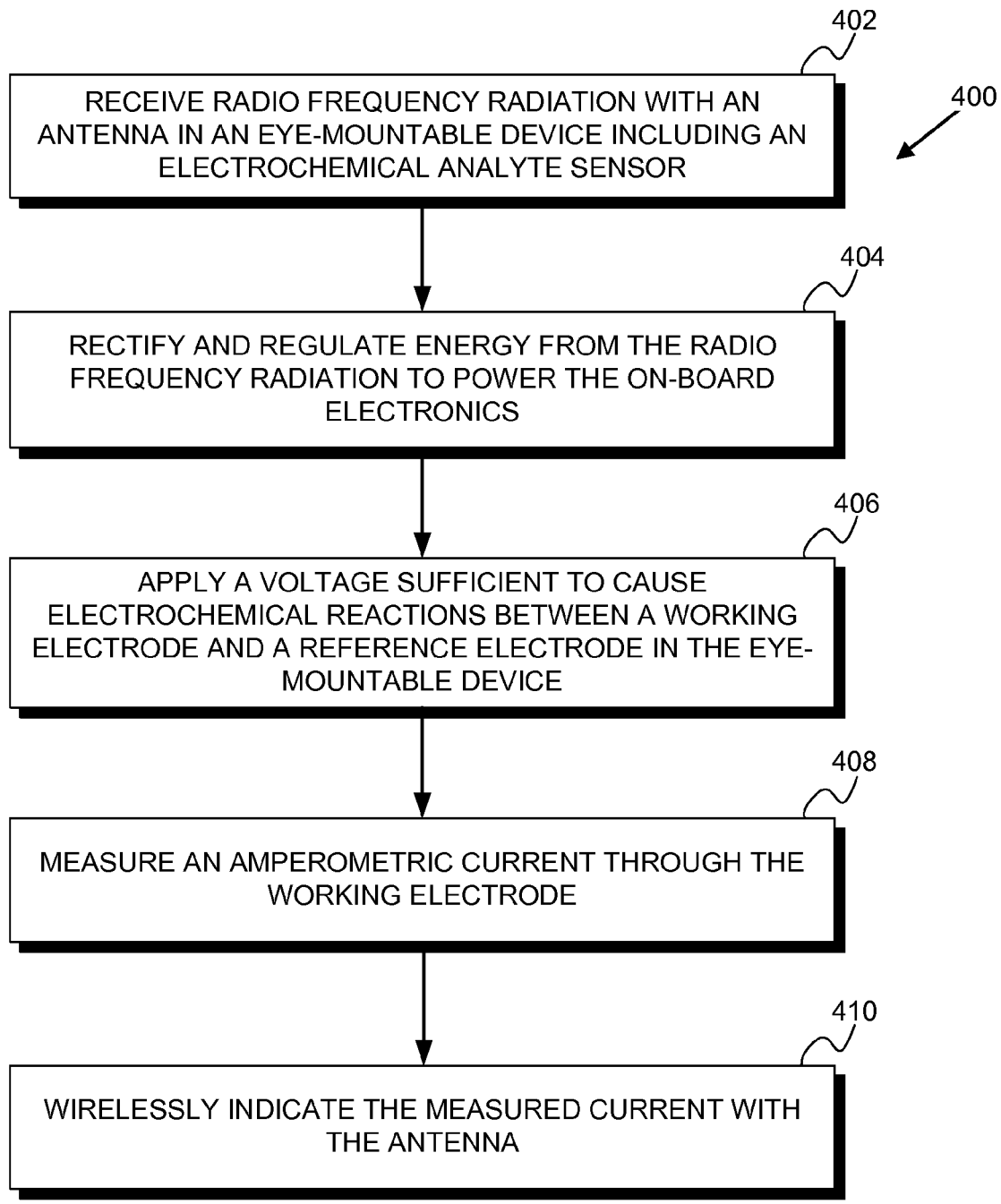
FIG. 4A is a flowchart of an example process for operating an amperometric sensor in an eye-mountable device to measure a tear film analyte concentration.

FIG. 4A is a flowchart of a process 400 for operating an amperometric sensor in an eye-mountable device to measure a tear film analyte concentration. Radio frequency radiation is received at an antenna in an eye-mountable device including an embedded electrochemical sensor (402). Electrical signals due to the received radiation are rectified and regulated to power the electrochemical sensor and associated controller (404). For example, a rectifier and/or regulator can be connected to the antenna leads to output a DC supply voltage for powering the electrochemical sensor and/or controller. A voltage sufficient to cause electrochemical reactions at the working electrode is applied between a working electrode and a reference electrode on the electrochemical sensor (406). An amperometric current is measured through the working electrode (408). For example, a potentiostat can apply a voltage between the working and reference electrodes while measuring the resulting amperometric current through the working electrode. The measured amperometric current is wirelessly indicated with the antenna (410). For example, backscatter radiation can be manipulated to indicate the sensor result by modulating the antenna impedance.

Figure 4B:
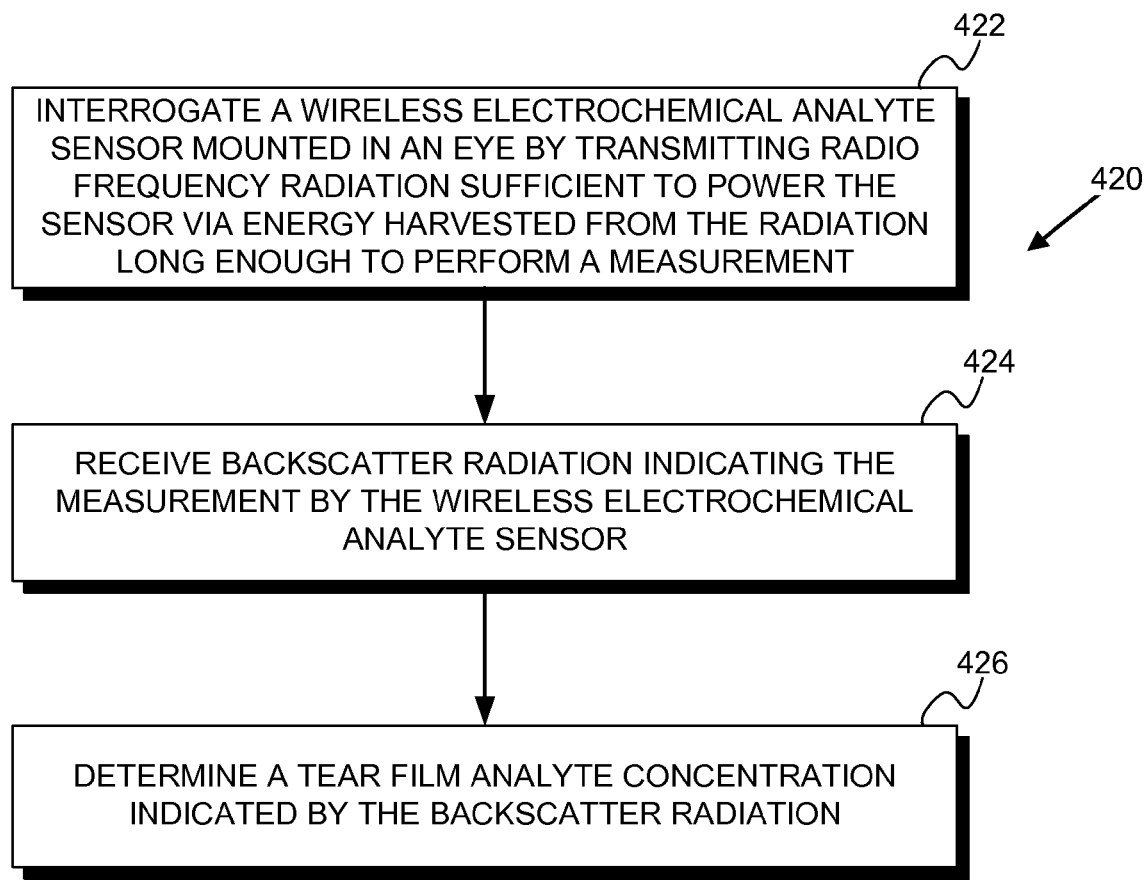
FIG. 4B is a flowchart of an example process for operating an external reader to interrogate an amperometric sensor in an eye-mountable device to measure a tear film analyte concentration.

FIG. 4B is a flowchart of a process 420 for operating an external reader to interrogate an amperometric sensor in an eye-mountable device to measure a tear film analyte concentration. Radio frequency radiation is transmitted to an electrochemical sensor mounted in an eye from the external reader (422). The transmitted radiation is sufficient to power the electrochemical sensor with energy from the radiation for long enough to perform a measurement and communicate the results (422). For example, the radio frequency radiation used to power the electrochemical sensor can be similar to the radiation 341 transmitted from the external reader 340 to the eye-mountable device 310 described in connection with FIG. 3 above. The external reader then receives backscatter radiation indicating the measurement by the electrochemical analyte sensor (424). For example, the backscatter radiation can be similar to the backscatter signals 343 sent from the eye-mountable device 310 to the external reader 340 described in connection with FIG. 3 above. The backscatter radiation received at the external reader is then associated with a tear film analyte concentration (426). In some cases, the analyte concentration values can be stored in the external reader memory (e.g., in the processing system 346) and/or a network-connected data storage.

For example, the sensor result (e.g., the measured amperometric current) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to an amperometric current value. The amperometric current value is approximately proportionate to the tear film analyte concentration with a sensitivity (e.g., scaling factor) relating the amperometric current and the associated tear film analyte concentration. The sensitivity value can be determined in part according to empirically derived calibration factors, for example.

While the body-mountable device has been described as comprising the eye-mountable device 110, 210, 310, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 310. For instance, the tooth-mountable device could include a polymeric material or a transparent polymer that is the same or similar to any of the polymeric materials or transparent polymers described herein and a substrate or a structure that is the same or similar to any of the substrates or structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 310. For instance, the skin-mountable device could include a polymeric material or a transparent polymer that is the same or similar to any of the polymeric materials or transparent polymers described herein and a substrate or a structure that is the same or similar to any of the substrates or structures described herein. With such an arrangement, the skin-mountable device may be configured to detect at least one analyte in a fluid (e.g., perspiration, blood, etc.) of a user wearing the skin-mountable device.

IV. Example Container

An eye-mountable device, such as the device described above, may need to be hydrated, sterilized, and/or calibrated before insertion into a user's eye. However, long-term storage in an aqueous solution may cause problems with the various electronic components of the eye-mountable device. Thus, a container that separates an aqueous solution from the eye-mountable device may be desirable.

Figure 5A:
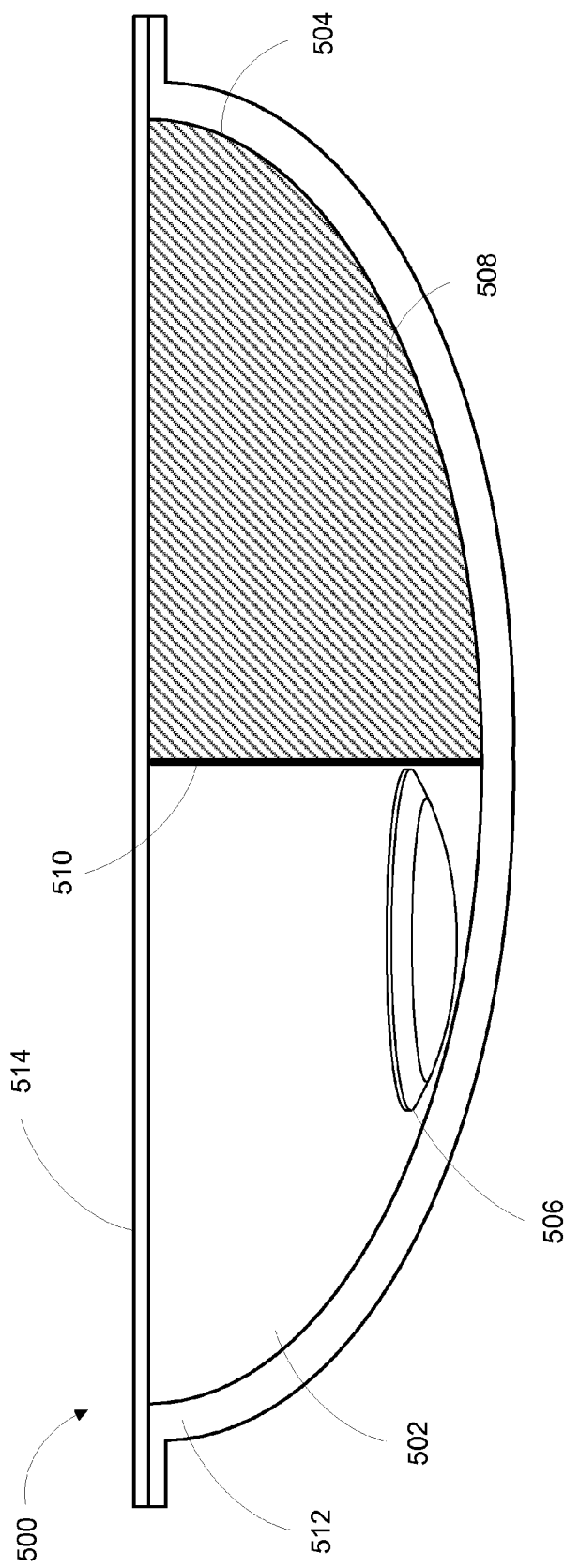
FIG. 5A is a cross-section view of an example container having a side-by-side configuration.

FIG. 5A illustrates a cross-section view of an example embodiment of a container 500. The container 500 may include a first chamber 502 and a second chamber 504. As shown in FIG. 5A, the first chamber 502 and the second chamber 504 may be arranged in a side-by-side configuration. The first chamber 502 may include an eye-mountable device 506, and the second chamber 504 may contain an aqueous solution 508. The eye-mountable device 506 may be similar to the eye-mountable devices 110, 210, 310 discussed above in connection with FIGS. 1-3 above and may include an analyte sensor embedded within a polymeric material configured to be contact-mounted to an eye.

The aqueous solution 508 may be a preconditioning solution used to hydrate the eye-mountable device 506 before insertion into a user's eye. In another example, the aqueous solution 508 may be a sterilization and/or a disinfecting solution used to clean the eye-mountable device 506 of any debris that has accumulated on the device during shipment and storage. In another example, the aqueous solution 508 may be a multipurpose solution used to hydrate and sterilize the eye-mountable device 506 before insertion into a user's eye.

In yet another example, the eye-mountable device 506 may include an analyte sensor embedded in the eye-mountable device 506. In such an embodiment, the aqueous solution 508 may be a calibration solution used to calibrate the analyte sensor. The analyte sensor embedded in the eye-mountable device 506 can be exposed to the calibration solution having a known analyte concentration and a sensor reading may be obtained while the analyte sensor remains exposed. The sensor result (e.g., the amperometric current) divided by the concentration of the analyte can be set as the sensitivity of the ophthalmic sensing platform, and a linear relationship can be established with the sensitivity as the slope to relate future and/or past sensor results to analyte concentrations. A technique can be used to determine a functional relationship relating the amperometric current and the concentration of analyte using only one calibration data point. For example, a single calibration data point (e.g., sensor result while the sensor is exposed to the calibration solution with a known analyte concentration paired with the known analyte concentration) can be used in combination with assumptions and/or previous calibration data to determine a functional relationship relating sensor results to analyte concentrations.

The functional form can be determined by solving for a linear relationship that passes through the calibration data point and the origin. Thus, the relationship is assumed to be linear, and a zero current reading is assumed to correspond to an analyte concentration of zero. The determination of the relationship then amounts to solving for the slope of such a linear relationship where the intercept is held fixed (e.g., at zero). The functional form of such a relationship in terms of the measured amperometric current ($I_{meas}$) is then:

$$AC = f(I_{meas}) = (AC_{cal}/I_{cal})I_{meas},$$

where $AC_{cal}$ is the analyte concentration of the calibration solution, and $I_{cal}$ is the sensor current measured while the eye-mountable analyte sensor is exposed the calibration solution. The slope of the linear relationship is therefore the sensitivity of the eye-mountable analyte sensor: $AC_{cal}/I_{cal}$. It is noted that the intercept can be assumed to be another value other than zero while still solving for the slope of a linear relationship. For example, an analyte concentration of zero can still register a low level amperometric current due to, for example, ions, enzymes, etc. that electrochemically react with the sensor even in the absence of the analyte. Moreover, in some embodiments, a linear relationship can be determined by using the calibration data point to solve for an intercept value (e.g., current level for zero analyte concentration) of a linear relationship while keeping the slope (e.g., sensitivity) of the relationship fixed. Other potential aqueous solutions are possible as well.

Referring back to FIG. 5A, the container 500 may also include a membrane 510 positioned between the first chamber 502 and the second chamber 504. The membrane 510 may include a thin polymeric material. The polymeric material may include polyolefin. Other materials are possible as well. In one embodiment, the thickness of the membrane 510 is less than about 250 micrometers or may be other thicknesses greater than 250 micrometers depending on a scale/size of the container 500. The container 500 may also include external surfaces 512 that define the general shape of the container 500. In FIG. 5A, the external surfaces 512 are shown in a semi-elliptical shape. In another embodiment, the external surfaces may be hemispherical or rectangular in shape. Other shapes are possible as well. The external surfaces 512 may include a polymer material. The polymeric material of the external surfaces 512 may be the same or different than the polymeric material of the membrane 510. In one embodiment, the thickness of the external surfaces 512 of the container 500 may be at least 10 times greater than the thickness of the membrane 510. The external surfaces 512 on the container 500 may be more rigid than the membrane 510, so as to protect the eye-mountable device 506 from forces applied during shipment and storage.

The container may also include a lid 514 configured to seal one or more of the first chamber 502 and the second chamber 504. The lid 514 may include a polyester spin cast woven fabric, although other materials are possible as well. In some embodiments, the lid 514 may be connected to the membrane 510. The lid 514 is configured to be removed by a user to access the eye-mountable device 506. The lid 514 ensures that the eye-mountable device 506 and aqueous solution 508 remain sealed in the container 500 during shipment and storage.

The membrane 510 is configured to rupture based on the application of a force to the container 500. The ruptured membrane 510 allows the aqueous solution 508 to engage with the eye-mountable device 506 to hydrate, sanitize and/or calibrate the eye-mountable device 506 before insertion into a user's eye, as discussed above. In one embodiment, the membrane 510 may be pre-stressed so as to weaken the membrane and therefore make it easier for a user to rupture the membrane. For example, a tensile stress may be applied to the membrane 510 during fabrication of the container 500. Other examples are possible as well.

Figure 5B:
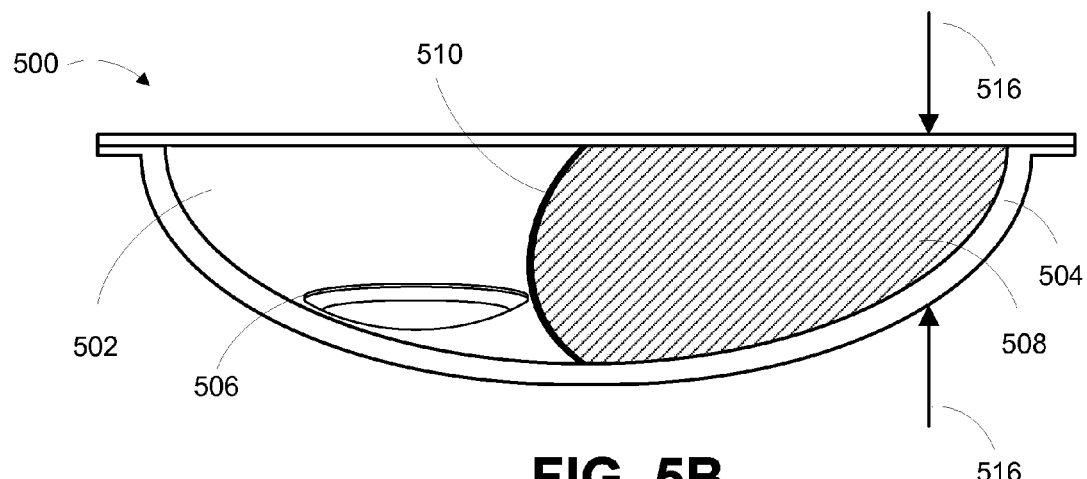
FIG. 5B is a cross-section view of an application of a force to the container according to an example embodiment.
Figure 5C:
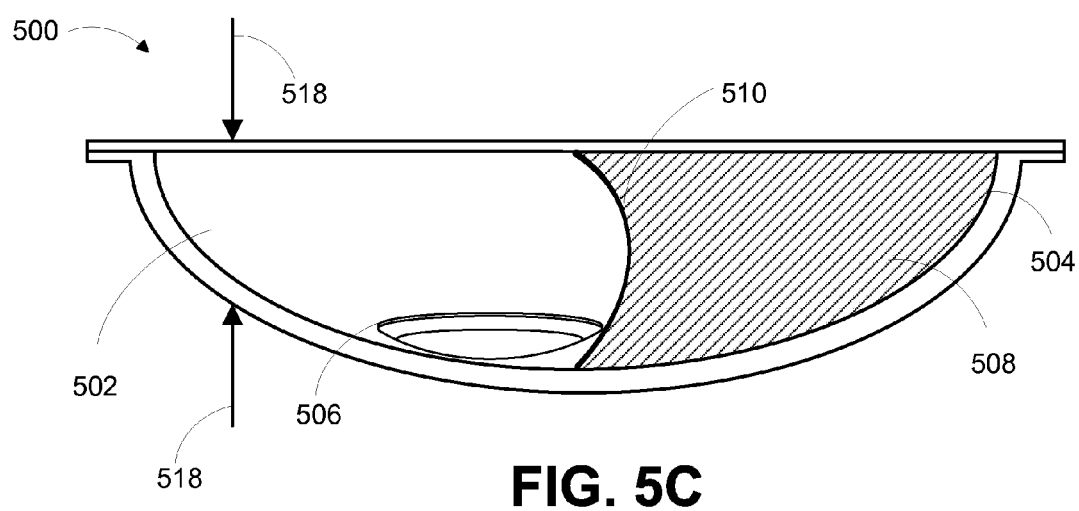
FIG. 5C is a cross-section view of an application of a force to the container according to another example embodiment.

In one embodiment, the membrane 510 may be ruptured by squeezing the container 500. FIGS. 5B and 5C illustrate examples of such an embodiment. In FIG. 5B, a force 516 is applied to the second chamber 504 of the container 500. The arrows denoting the force 516 may represent the index finger and the thumb of a user who squeezes the container 500. When the force 516 is applied to the second chamber 504, the pressure in the second chamber 504 increases, causing the membrane 510 to expand towards the first chamber 502. When a critical value of force 516 is applied, the membrane 510 will rupture, allowing the aqueous solution 508 to engage with the eye-mountable device 506.

FIG. 5C illustrates a similar embodiment, except the force 518 is applied to the first chamber 502 of the container 500. When the force 518 is applied to the first chamber 502, the pressure in the first chamber 502 increases, causing the membrane 510 to expand. When a critical value of force 518 is applied, the membrane 510 will rupture, allowing the aqueous solution 508 to engage with the eye-mountable device 506.

The critical force may be a value greater than those forces typically experienced in shipment and storage, but less than about 25 Newtons.

Figure 5D:
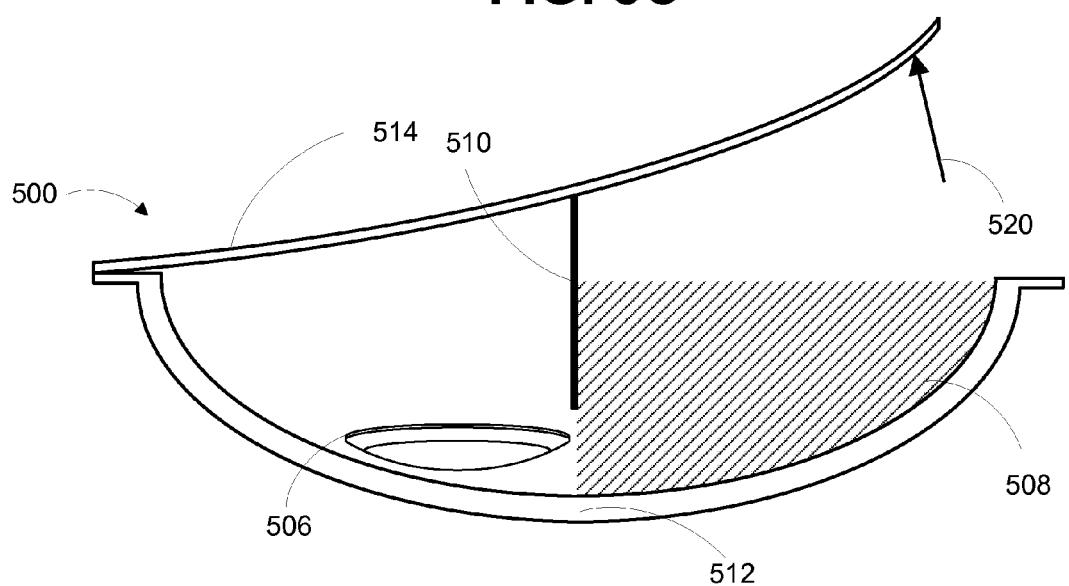
FIG. 5D is a cross-section view of an application of a force to the container according to yet another example embodiment.

In another embodiment, the membrane 510 may be connected to the lid 514 of the container 500, and the membrane 510 may be ruptured when a user removes the lid 514. FIG. 5D illustrates such an embodiment. As the lid 514 is removed by the user through application of force 520, the membrane 510 may remain connected to the lid 514 and become disconnected from the bottom external surface 512 of the container 500. The ruptured membrane 510 allows the aqueous solution 508 to engage with the eye-mountable device 506. In one embodiment, an adhesive may be used to connect the membrane 510 to the lid 514. In another embodiment, the lid 514 and the membrane 510 may be fabricated together as one piece. In yet another embodiment, the membrane 510 may be perforated so that when the lid 514 is removed, the membrane 510 ruptures at the perforation. Other embodiments are possible as well.

In yet another embodiment, the membrane 510 may be ruptured by shaking the container 500. The act of shaking the container 500 may increase the pressure in one or more of the first chamber 502 and the second chamber 504, thereby applying a force to the membrane 510. When a critical value of force is applied, the membrane 510 will rupture, allowing the aqueous solution 508 to engage with the eye-mountable device 506.

In yet another embodiment, a user may remove the lid 514, and then remove the membrane 510 by hand. In one example, the membrane 510 may be perforated and the user may rupture the membrane 510 by tearing the perforation. In another example, the user may simply peel away the membrane 510 after removing the lid 514 to allow the aqueous solution 508 to engage with the eye-mountable device 506. Other embodiments of applying a force to rupture the membrane are possible as well.

Figure 6:
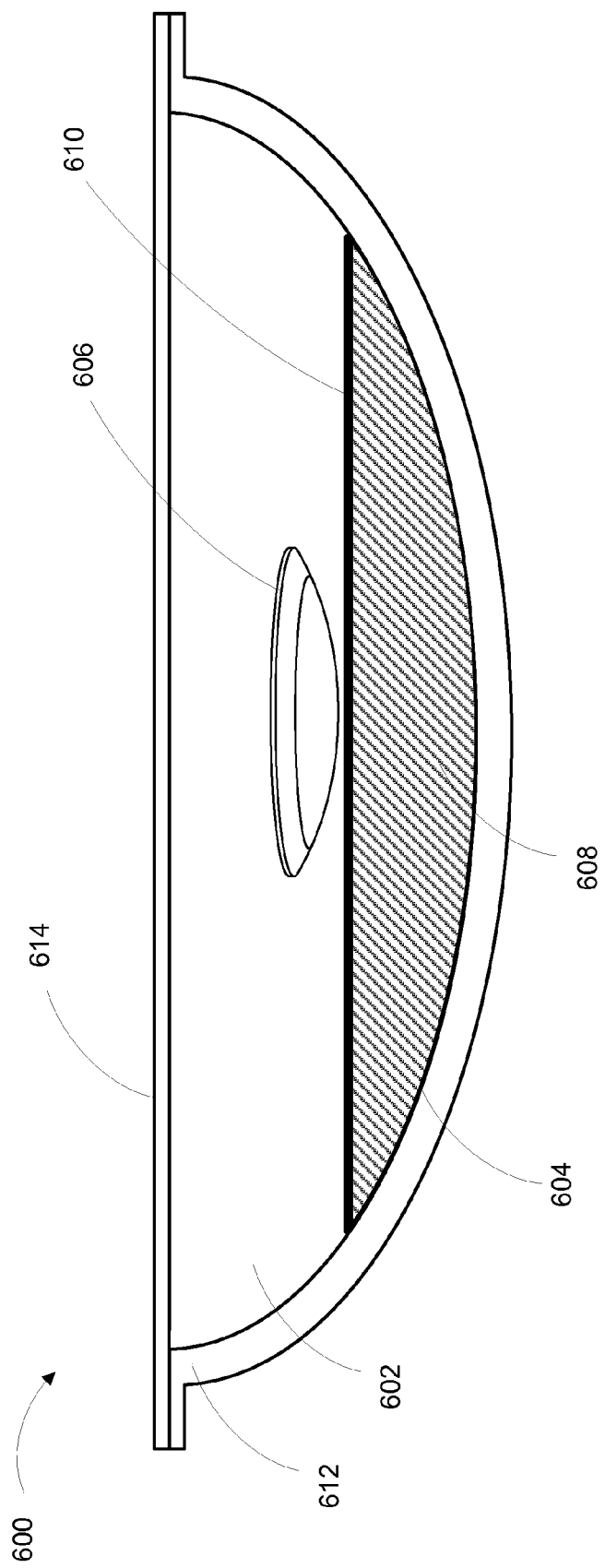
FIG. 6 is a cross-section view of an example container having a top-bottom configuration.

FIG. 6 illustrates a cross-section view of another embodiment of a container 600. In this embodiment, the first chamber 602 and the second chamber 604 are arranged in a top-bottom configuration. Similar to the configuration described above in reference to FIG. 5A, the first chamber 602 may include an eye-mountable device 606, and the second chamber 604 may include an aqueous solution 608. The eye-mountable device 606 may be similar to the eye-mountable devices 110, 210, 310 discussed above in connection with FIGS. 1-3 above and may include an analyte sensor embedded within a polymeric material configured to be contact-mounted to an eye. The container 600 may also include a membrane 610 positioned between the first chamber 602 and the second chamber 604 and may also include external surfaces 612 that define the general shape of the container 600. The container 600 may also include a lid 614 configured to seal the first chamber 602. As discussed above, the membrane 610 may be configured to rupture based on the application of a force to the container 600. The membrane 610 may be ruptured by squeezing the container 600 or by shaking the container 600, as described above. In another embodiment, the membrane 610 may be connected to the lid 614 of the container 600, and the membrane 610 may be ruptured when a user removes the lid 614. Other embodiments of applying a force to rupture the membrane are possible as well. As shown in FIG. 6, the second chamber 604 containing the aqueous solution 608 may be positioned below the first chamber 602 containing the eye-mountable device 606. In another embodiment, the first chamber 602 may be positioned below the second chamber 604.

Figure 7:
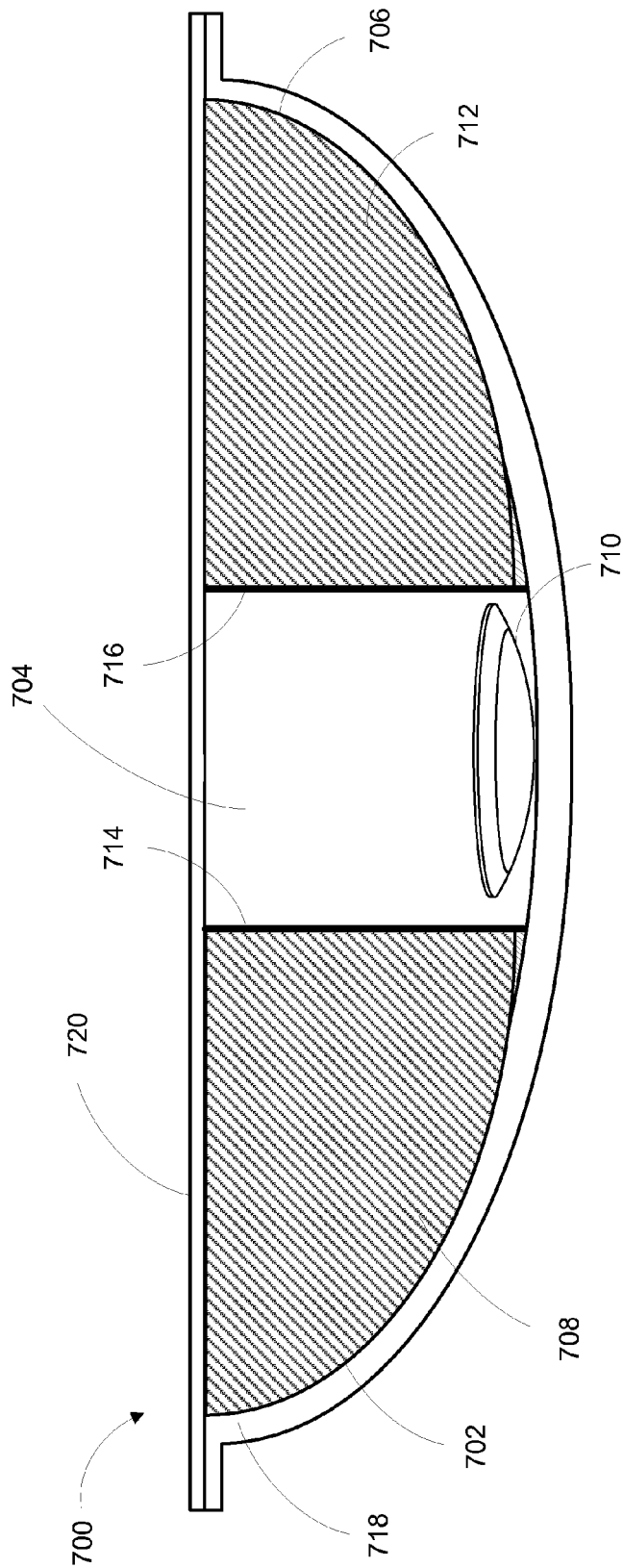
FIG. 7 is a cross-section view of an example container having a third chamber.

FIG. 7 illustrates a cross-section view of another embodiment of a container 700. In this embodiment, the container 700 may include a first chamber 702, a second chamber 704, and a third chamber 706. The first chamber 702 may include a first aqueous solution 708, the second chamber may contain an eye-mountable device 710, and the third chamber 706 may contain a second aqueous solution 712. The eye-mountable device 710 may be similar to the eye-mountable devices 110, 210, 310, 506 discussed above in connection with FIGS. 1-3, and 5 above and may include an analyte sensor embedded within a polymeric material configured to be contact-mounted to an eye.

The first aqueous solution 708 may be a preconditioning solution used to hydrate the eye-mountable device 710 before insertion into a user's eye. In another example, the first aqueous solution 708 may be a sterilization and/or a disinfecting solution used to clean the eye-mountable device 710 of any debris that has accumulated on the device during shipment and storage. In another example, the first aqueous solution 708 may be a multipurpose solution used to hydrate and sterilize the eye-mountable device 710 before insertion into a user's eye. In one embodiment, the second aqueous solution 712 may be the same as the first solution 708. In another embodiment, the second aqueous solution 712 may be different than the first solution 708.

The container 700 may also include a first membrane 714 positioned between the first chamber 702 and the second chamber 704, and a second membrane 716 positioned between the second chamber 704 and the third chamber 706. The first membrane 714 may include a thin polymeric material. The polymeric material may include polyolefin. Other materials are possible as well. The second membrane 716 may include the same material as the first membrane 714. In another example, the second membrane 716 may include different materials than the first membrane 716.

The container 700 may also include external surfaces 718 that define the general shape of the container 700. The container 700 may also include a lid 720 configured to seal the container 700. As discussed above, the first membrane 714 and/or the second membrane 716 may be configured to rupture based on the application of a force to the container 700. The first membrane 714 and/or the second membrane 716 may be ruptured by squeezing the container 700 or by shaking the container 700, as described above. In another embodiment, the first membrane 714 and/or the second membrane 716 may be connected to the lid 720 of the container 700, and the first membrane 714 and/or the second membrane 716 may be ruptured when a user removes the lid 720. Other embodiments of applying a force to rupture the membrane are possible as well.

V. Example Method

Figure 8:
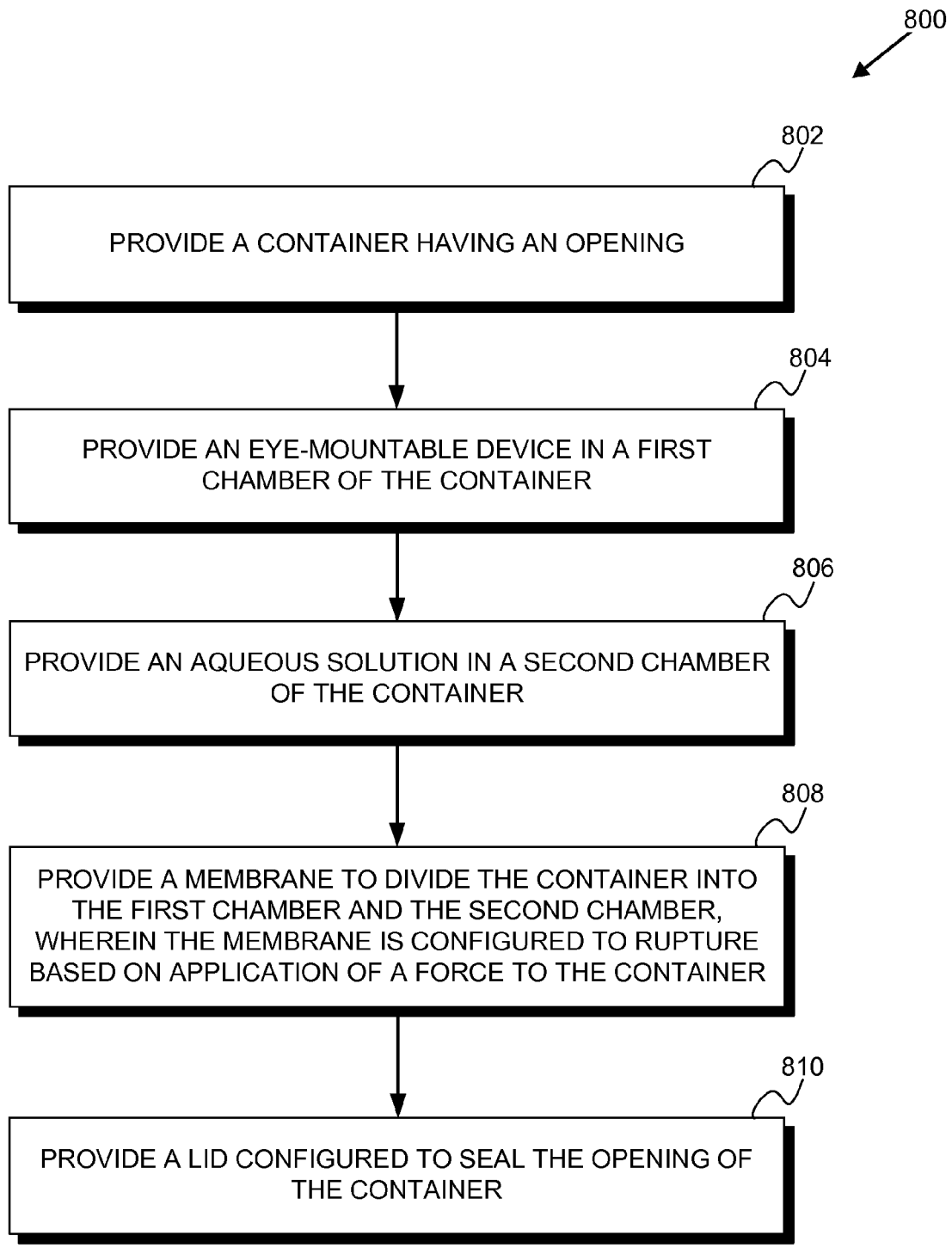
FIG. 8 is a flowchart, in accordance with an example embodiment.

FIG. 8 depicts a flowchart of an example method. Method 800 may include one or more operations, functions, or actions as illustrated by one or more of blocks 802-810. Although the blocks are illustrated in a sequential order, these blocks may also be performed in parallel, and/or in a different order than those described herein. Also, the various blocks may be combined into fewer blocks, divided into additional blocks, and/ or removed based upon the desired implementation.

For purposes of illustration, the method is described below in a scenario where a body-mountable device comprises an eye-mountable device. It should be understood, however, that the method 800 may involve scenarios where the body-mountable device comprises other mountable devices that are mounted to other portions of the human body. For example, method 800 may involve scenarios where the body-mountable device comprises a tooth-mountable device and/or a skin mountable device.

At block 802, the method includes providing a container having an opening. In one embodiment, providing the container with an opening may include forming the container through cast molding by compressing molding material between molding cavities. The molding material may include a polymeric material such as polyolefin, although other materials are possible as well. In another embodiment, the container may be formed via injection molding. In injection molding, molding material may be heated and injected or otherwise forced into a molding cavity or cavities. The injected molding material may then cool and harden to the configuration of the molding cavity or cavities. As another example, the container may be formed via spin casting. Through spin-casting techniques, a fabrication device may form a container having a precise thickness. In an example, a spin-casting mold may be spun along its central access at a set speed, and the molding material may be introduced to the mold as the mold is spinning in order to form the container. The final thickness of the container may be influenced by various factors, including but not limited to the spin-casting mold, the amount of molding material introduced to the spin-casting mold, properties of the molding material such as viscosity, and/or the speed at which the spin-casting mold is rotated. These factors may be varied in order to result in a container of a well-defined thickness. In yet another example, the container may be formed via thermoforming. Through thermoforming, a sheet of polymeric material is heated to a pliable forming temperature. The heated polymeric material may then be formed to a specific shape in a mold, and trimmed to create a usable container. Other embodiments are possible as well.

At block 804, the method includes providing an eye-mountable device in a first chamber of the container. The eye-mountable device may be similar to the eye-mountable devices 110, 210, 310 discussed above in connection with FIGS. 1-3 above and may include an analyte sensor embedded within a polymeric material configured to be contact-mounted to an eye.

At block 806, the method includes providing an aqueous solution in a second chamber of the container. The aqueous solution may be a preconditioning solution used to hydrate the eye-mountable device before insertion into a user's eye. In another example, the aqueous solution may be a sterilization and/or a disinfecting solution used to clean the eye-mountable device 506 of any debris that has accumulated on the device during shipment and storage. In another example, the aqueous solution may be a multipurpose solution used to hydrate and sterilize the eye-mountable device before insertion into a user's eye. In yet another example, the aqueous solution may be a calibration solution having a known analyte concentration which may be used to calibrate an analyte sensor embedded in the eye-mountable device. Other aqueous solutions are possible as well.

At block 808, the method includes providing a membrane to divide the container into the first chamber and the second chamber, wherein the membrane is configured to rupture based on application of a force to the container. The ruptured membrane enables the aqueous solution to engage with the eye-mountable device. The membrane may include a thin polymeric material, such as polyolefin. Other materials are possible as well. In one embodiment, the thickness of the membrane is less than about 100 micrometers. The ruptured membrane allows the aqueous solution to engage with the eye-mountable device to hydrate, sanitize and/or calibrate the eye-mountable device before insertion into a user's eye, as discussed above. In one embodiment, the membrane may be pre-stressed so as to weaken the membrane and therefore make it easier for a user to rupture the membrane. For example, a tensile stress may be applied to the membrane during fabrication of the container. Other examples are possible as well.

In one embodiment, the membrane may be ruptured by squeezing the container, as discussed above in relation to FIGS. 5B and 5C. In another embodiment, the membrane may be connected to a lid of the container, and the membrane may be ruptured when a user removes the lid, as discussed above in relation to FIG. 5D. In yet another embodiment, the membrane may be ruptured by shaking the container. Other embodiments of applying a force to rupture the membrane are possible as well.

At block 810, the method includes providing a lid configured to seal the opening of the container. The lid may include a polyester spin cast woven fabric, although other materials are possible as well. In some embodiments, the lid may be connected to the membrane. The lid is configured to be removed by a user to access the eye-mountable device. The lid ensures that the eye-mountable device and aqueous solution remain sealed in the container during shipment and storage.

VI. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. An apparatus comprising:
a cavity having an inner surface and an opening;
a membrane disposed within the cavity and extending from the inner surface to the opening;
wherein the membrane divides the cavity into a first chamber and a second chamber;
wherein the first chamber contains an eye-mountable device;
wherein the second chamber contains an aqueous solution;
wherein the membrane is configured to rupture based on application of a force to the apparatus, and wherein the ruptured membrane allows the aqueous solution to engage with the eye-mountable device; and
a lid configured to seal the opening.

2. The apparatus of claim 1, wherein the aqueous solution includes a preconditioning solution.

3. The apparatus of claim 1, wherein the aqueous solution includes a disinfecting solution.

4. The apparatus of claim 1, wherein the eye-mountable device contains an analyte sensor embedded in the eye-mountable device.

5. The apparatus of claim 4, wherein the aqueous solution includes a calibration solution, and wherein the calibration solution has a known analyte concentration.

6. The apparatus of claim 1, wherein the lid is connected to the membrane, and wherein one or more of the lid and the membrane are configured to be at least partially removed based on application of the force.

7. The apparatus of claim 1, wherein the first chamber is positioned adjacent to the second chamber.

8. The apparatus of claim 1, wherein the membrane is pre-stressed so as to weaken the membrane.

9. The apparatus of claim 1, wherein a thickness of the membrane is less than about 250 micrometers.

10. The apparatus of claim 1, wherein the membrane includes a polymeric material.

11. An apparatus comprising:
a container having external surfaces and a cavity therein, the cavity having an inner surface and an opening;
a membrane disposed within the cavity and extending from the inner surface;
wherein the membrane divides the cavity into a first chamber and a second chamber, wherein the first chamber contains an eye-mountable device, wherein the second chamber contains an aqueous solution, and wherein the membrane is configured to rupture based on application of a force to the apparatus to allow the aqueous solution to engage with the eye-mountable device; and
a lid configured to seal the opening.

12. The apparatus of claim 11, wherein a thickness of the external surfaces is at least about 10 times greater than a thickness of the membrane.

13. The apparatus of claim 11, wherein the membrane is pre-stressed so as to weaken the membrane.

14. The apparatus of claim 11, wherein the first chamber is positioned adjacent to the second chamber.

15. The apparatus of claim 11, wherein the first chamber is positioned above the second chamber.

16. A method comprising:
    providing a container having an inner surface, and an opening;
    providing an eye-mountable device in a first chamber of the container;
    providing an aqueous solution in a second chamber of the container;
    providing a membrane within the container to divide the container into the first chamber and the second chamber, wherein the membrane extends from the inner surface to the opening, and wherein the membrane is configured to rupture based on application of a force to the container to enable the aqueous solution to engage with the eye-mountable device; and
    providing a lid configured to seal the opening of the container.

17. The method of claim 16, further comprising applying a tensile stress to the membrane so as to weaken the membrane.

18. The method of claim 16, wherein the first chamber is positioned adjacent to the second chamber.

* * * * *